United States Patent [19]

Piesch et al.

[11] 4,320,060
[45] Mar. 16, 1982

[54] PROCESS FOR THE PREPARATION OF DERIVATIVES OF 3-(4-HYDROXY-ANILINO)CARBAZOLE

[75] Inventors: Steffen Piesch, Oberursel; Friedrich Engelhardt, Frankfurt am Main; Herbert Wille, Frankfurt am Main; Wolf Weidemüller, Frankfurt am Main; Artur Meyer, Schöneck, all of Fed. Rep. of Germany

[73] Assignee: Cassella Aktiengesellschaft, Frankfurt, Fed. Rep. of Germany

[21] Appl. No.: 108,486

[22] Filed: Dec. 31, 1979

[30] Foreign Application Priority Data

Jan. 8, 1979 [DE] Fed. Rep. of Germany ........... 29441

[51] Int. Cl.³ .......................................... C07D 209/88
[52] U.S. Cl. .................................................. 260/317
[58] Field of Search ........................................ 260/317

[56] References Cited

FOREIGN PATENT DOCUMENTS 230119 12/1908 Fed. Rep. of Germany ...... 260/317

OTHER PUBLICATIONS

Horgna et al., *Chem. Abstracts*, vol. 60, (1964), column 506(a).
Smith, *The Chemistry of Open-Chain Organic Nitrogen Compds.*, vol. I, (1965), p. 121.

*Primary Examiner*—Henry R. Jiles
*Assistant Examiner*—R. W. Romsuer
*Attorney, Agent, or Firm*—Connolly and Hutz

[57] ABSTRACT

The process for the preparation of a 3-(4-hydroxyanilino)carbazole of the formula

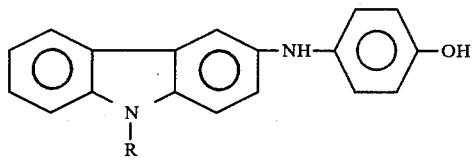

wherein R is hydrogen, alkyl having 1 to 8 carbon atoms or halogenoalkyl having 1 to 8 carbon atoms, comprising reacting a 3-aminocarbazole of the formula

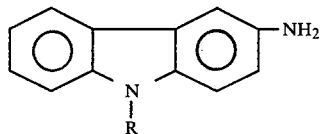

with p-hydroquinone or p-aminophenol or a mixture of p-hydroquinone and p-aminophenol in at least stoichiometric amounts by heating to a temperature of 150° to 300° C. with exclusion of oxygen.

8 Claims, No Drawings

PROCESS FOR THE PREPARATION OF DERIVATIVES OF 3-(4-HYDROXY-ANILINO)CARBAZOLE

The invention relates to a process for the preparation of derivatives of 3-(4-hydroxy-anilino)-carbazole of the general formula

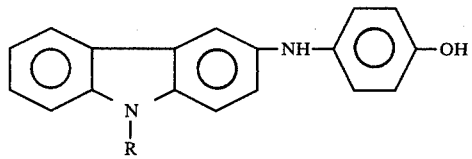

wherein R denotes hydrogen, alkyl with 1 to 8 C atoms or halogenoalkyl with 1 to 8 C atoms, the derivatives of the general formula I prepared by the process according to the invention and their use for the preparation of sulphur dyestuffs.

The compounds of the general formula I are also called, inter alia, carbazolyl-3- aminophenols or leuco-compounds of carbazole-indophenols. The carbazole-indophenols and the compounds of the general formula I are indispensable starting materials for the preparation of valuable sulphur dyestuffs of a predominantly blue shade. The compounds of the formula I have hitherto been prepared by reducing the corresponding carbazoleindophenols (carbazolyl-3-iminoquinones or 1,4-benzoquinone mono-(carbazolyl-3-imides)), for the preparation of which essentially two processes have hitherto been disclosed:

1. By condensation of carbazole or of N-substituted carbazoles with p-nitrosophenol in cold, highly concentrated sulphuric acid, whilst cooling (French Pat. No. 457,535 and German Reichspatent Specifications Nos. 218,371, 224,951 and 230,119).

2. By reaction of carbazole and its derivatives with p-aminophenol in concentrated sulphuric acid in the presence of an oxidising agent, such as manganese dioxide, whilst cooling (French Pat. No. 457,535).

Subsequent reduction of the carbazole-indophenols to give the compounds of the general formula I is in general carried out with iron in dilute acid.

3. To prepare certain derivatives of the compounds of the general formula I, it is also known (French Pat. No. 390,715) to reduce certain derivatives of 2,2'-dinitrodiphenyl and to bring about cyclisation to give the carbazole derivative by treatment with dilute, boiling mineral acids.

On page 315 of O. Lange "Die Zwischenprodukte der Teerfarbenfabrikation" ("The Intermediate Products of Coal-Tar Dye Manufacture"), Leipzig 1920, German Patent Application No. A 25 495, Class 12 P, of 24.2.1914 is referred to, in which the preparation of indophenols and their leuco-compounds from 3-aminocarbazole or its N-substituted derivatives by condensation with hydroquinone in the presence of dehydrating agents, avoiding oxidation, is said to be described. The Application has not been published, so that details of this process are not known. On carrying out the reaction in the presence of the dehydrating agents known at that time, namely concentrated sulphuric acid or zinc chloride, working up by water is unavoidably necessary and the leucoindophenol is obtained only in low yield, in addition to a number of undesired by-products. Purification of the leuco-indophenols thus obtained is difficult and excludes application of this process for the industrial preparation of the desired products. The known preparation processes mentioned above under 2. and 3. also do not give the desired indophenols or leuco-indophenol in the desired yield and purity, and over the long period for which they have been known, could not be improved to the extent such that they can be carried out on an industrial scale. The condensation process mentioned above under 1, in which p-nitrosophenol is first subjected to a condensation reaction with the carbazole derivative and the resulting quinoidal intermediate product of the indophenol must then as a rule be reduced since the quinoidal product is particularly unstable, has hitherto asserted itself as the optimum known process in industry.

This known process has serious technical disadvantages. On the one hand, the process products are not obtained in uniform quality. Rather, the quality of the indophenols obtained varies as a result of slight deviations, which cannot be controlled precisely, in the process or slight deviations in the quality of the starting materials or of the iron used for the reduction, which manifests itself in the different result for the quality of the sulphur dyestuffs prepared from the indophenols. In addition, large amounts of sulphuric acid are required for carrying out this process, and at present these must either be worked up again or removed in another manner which raises no ecological objections. The preparation of the p-nitrosophenol required as a starting material for this process is also associated with considerable difficulties of an ecological nature. Moreover, p-nitrosophenol is unstable to heat and its quality changes with the time of storage.

In spite of all the difficulties mentioned for the processes known hitherto and in spite of the intensive search, which has lasted for decades, for improvements to the processes, the condensation of carbazoles with p-nitrosophenol has hitherto been regarded as the optimum industrial preparation process for the desired indophenols and leuco-indophenols to date. It has now been found, surprisingly, that the disadvantages and difficulties of the processes known hitherto for the preparation of leucoindophenols of the general formula I can be avoided and these products can be prepared in a simple manner and in very good yield and high purity.

The process according to the invention for the preparation of compounds of the general formula I is characterised in that a 3-aminocarbazole of the general formula

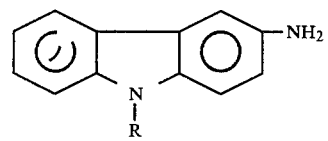

and p-hydroquinone or p-aminophenol or a mixture of p-hydroquinone and p-aminophenol in at least stoichiometric amounts are heated to temperatures of 150° to 300° C., appropriately to 170° to 230° C., with exclusion of oxygen. In the simplest case of carrying out the process according to the invention, the participants in the reaction are melted together, optionally with p-hydroquinone or p-aminophenol in excess, and are kept at the condensation temperature of between 150° and 250° C., preferably at 170° to 230° C., until no further water of reaction or ammonia is distilled off from the batch. The reaction has as a rule virtually ended after 2 to 10 hours, depending on the chosen reaction temperature. In the simplest case, the reaction mixture is worked up by distilling off the excess of p-hydroquinone and/or p-aminophenol, appropriately under reduced pressure, then draining off the melt out of the reaction vessel and subsequently comminuting the product in a suitalbe mill. However, for the purpose of purification, it is also possible to distill the compound of the formula I formed, and this can be effected directly, from the reaction vessel. This distillation is appropriately carried out under reduced pressure. It was exceptionally surprising that the compounds of the formula I, which have hitherto been regarded as exceptionally sensitive compounds which readily decompose, can be purified in a very simple way by such a preparation and distillation. Virtually no decomposition takes place, even at bottom temperatures of 300° C. and above.

The condensation reaction between the aminocarbazoles of the formula II and p-hydroquinone or p-aminophenol can be accelerated significantly by adding a catalytic amount of iodine, and in addition this leads to purer products. Additions of 0.1 to 4, preferably 0.1 to 1, % by weight, relative to the carbazole derivative of the general formula II employed, are usually regarded as catalytic amounts. Since the addition of iodine interferes neither with the working up of the leuco-indophenols prepared according to the invention nor with their further processing, it is preferable to carry out the process according to the invention with the addition of catalytic amounts of iodine.

The condensation, according to the invention, of p-hydroquinone and/or p-aminophenol with the carbazole derivative of the formula II can also be carried out in the presence of an inert organic solvent. Those solvents which have boiling points above the condensation temperature, that is to say in particular above 150° to 230° C., are appropriately used. If, on the basis of particular considerations, solvents which have boiling points below 150° C. are to be employed, it is appropriate to carry out the process in a vessel (autoclave) which is sealed pressure-tight. Examples of organic solvents which are suitable for carrying out the process according to the invention are petroleum fractions with a boiling point above 150° C., cyclic hydrocarbons, such as, for example, decalin, or aromatic solvents, in particular a technical grade mixture of monochlorobenzene and dichlorobenzene. The condensation, according to the invention, of p-hydroquinone and/or p-aminophenol with a carbazole derivative of the general formula II can also be carried out in the presence of a solvent of the general formula III or IV

$$R^1O-(CH_2CH_2O)_n-R^1 \quad (III)$$

$$R^1O-(CH_2CH_2O)_n-H \quad (IV)$$

wherein $R^1$ denotes $-CH_3$, $-C_2H_5$ or $-C_3H_7$ and n denotes 1, 2 or 3, or in a higher alcohol or alkanol ether, especially if the leucoindophenols prepared are then converted into sulphur dyestuffs in a so-called boiling melt, that is to say a solution of sodium polysulphides. Examples of suitable solvents of the general formulae III and IV are diglycol dimethyl ether, diglycol diethyl ether, glycol diethyl ether, ethylene glycol monomethyl ether, mono-ethyl ether or mono-propyl ether and diethylene glycol mono-methyl ether or mono-propyl ether. If solvents of the general formula III or IV are used, or in a higher alcohol or alkanol ether, the crude reaction mixture of the leuco-indophenol can be directly subjected to sulphurizing.

If the preparation of the compounds of the general formula I by the process according to the invention is carried out in the preferred temperature range of 170° to 230° C. in the presence of an inert solvent, this solvent should appropriately have a boiling point of 180° to 240° C. or more under normal pressure. An inert solvent of this type which is immiscible with water at normal temperature is appropriately chosen. In the reaction of the carbazole derivative II with p-hydroquinone, such inert solvents act as azeotropic entraining agents for the water split off during the reaction. Examples of such solvents which are suitable as azeotropic entraining agents are decalin, monochlorobenzene and dichlorobenzene.

When an inert solvent is used, the amount thereof should be kept as low as possible. As a rule, it is not necessary to employ more than 15% by weight of inert solvent, relative to the total weight of the reactants.

In the reaction of the compound of the general formula II with p-hydroquinone and/or p-aminophenol, exclusion of oxygen is effected, for example, by carrying out the reaction under an atmosphere of an inert gas, such as, for example, nitrogen. It is appropriate to employ at least 1.3 times the stoichiometric amount of p-hydroquinone and/or p-aminophenol and preferably at least 1.6 times the stoichiometric amount of hydroquinone and/or p-aminophenol, especially if no inert solvent is used. In this case, the p-aminophenol or the p-hydroquinone or the mixture of these substances acts as the solvent. Larger excesses of p-hydroquinone and/or p-aminophenol than 3 times the stoichiometric amount do not usually need to be employed. When the reaction has ended, the excess p-aminophenol and/or p-hydroquinone can easily be distilled off, appropriately under reduced pressure, and can be re-used in a further batch.

In carrying out the reaction between the carbazole derivative of the general formula II and p-hydroquinone or p-aminophenol, the course of the reaction can be followed either by thin layer chromatography or, if p-hydroquinone is used, by determination of the water split off, or, if p-aminophenol is used, by titrimetric determination of the ammonia split off.

p-Hydroquinone and p-aminophenol are known substances. Most of the 3-aminocarbazoles of the general formula II are also known. The compounds of the general formula II in which R=alkyl can easily be obtained, for example by alkylating carbazole on the nitrogen, for example using dialkylsulphates or alkyl halides, subsequently introducing a nitro group in the 3-position by nitration and then reducing this group to the $-NH_2$ group in a known manner.

The alkyl radicals R contained in the leuco-indophenols of the formula I which can be prepared according to the invention can be linear or branched, or also substituted by halogen. Examples of alkyl radicals R are methyl; ethyl; prop-1-yl or -2-yl; but-1-yl or -2-yl; 2-methyl-prop-1-yl or -2-yl; pent-1-yl, -2-yl or -3-yl; 2-methyl-but-1-yl, -2-yl or -3-yl; hex-1-yl, -2-yl or -3-yl; 2- or 3-methyl-hex-1-yl, -2-yl or -3-yl; 2-ethyl-but-1-yl, -2-yl or -3-yl; heptyl, isoheptyl, octyl, 2-ethyl-hex-1-yl, -2-yl or -3-yl; 3-ethyl-hex-1-yl, -2-yl or -3-yl; β-chloroethyl and γ-chloropropyl.

The process of the present invention is preferably used for the preparation of leuco-indophenols of the formula I in which R denotes hydrogen or alkyl with 1 to 4 C atoms, in particular ethyl.

If the leuco-indophenols of the formula I prepared according to the invention are purified by subsequent vacuum distillation, sulphur dyestuffs which, compared with corresponding sulphur dyestuffs which have been obtained from conventionally prepared leuco-indophenols of the formula I, have an increased brilliance and increased clarity of shade, can be prepared therefrom by the sulphurizing processes hitherto customary. In this connection, it should be emphasised in particular that indophenols of the formula I which have been prepared by processes known hitherto, in particular by condensation of carbazoles with p-nitrosophenol in $H_2SO_4$, cannot be distilled without decomposition and in addition, on prolonged storage at moderately elevated temperature, are increasingly converted into decomposition products which can no longer be sulphurized.

Vacuum distillation, for example under 0.1 to 0.6 mbar, of the leuco-indophenols prepared according to the invention presents no technical difficulties. 3-(4-Hydroxy-anilino)-9-ethyl-carbazole has, for example, a boiling point of 265° to 282° C. under 0.25 to 0.55 mbar, and 3-(4-hydroxy, anilino)-carbazole has, for example, a boiling point of 310° to 320° C. under 0.13 mbar.

The process according to the invention is simple to carry out industrially. It produces excellent yields, in particular a very good space/time yield, above all in the case of the preferred embodiment with the addition of iodine, it necessitates no troublesome measures for isolation of the reaction product, virtually no effluents, waste solvents or other ecologically unacceptable waste products are formed and products of hitherto unachievable purity which can be used for the preparation of sulphur dyestuffs, the shade and purity of colour of which are excellent and always reproducible, can be obtained, above all in the case of the preferred embodiment with the addition of iodine. With regard to the various methods of further processing the leucoindophenols of the formula I prepared, the procedure of the process according to the invention without any solvent is very generally applicable.

As a rule, purification by distillation is not necessary for further processing of the leuco-indophenols of the formula I, prepared according to the invention, by known sulphurizing processes, but the melt can be directly subjected to known sulphurizing operations, after comminution.

The leuco-indophenols prepared according to the invention are sulphurized in a baked melt or boiling melt in a manner which is in itself known. These sulphurizing processes are described, for example, in "Venkataraman, The Chemistry of Synthetic Dyes, Volume 2 (1952), page 1,062 et seq. and page 1,103 et seq, and Volume 7 (1974), page 24 et seq, Academic Press, New York, San Francisco, London", and in BIOS report 983 pages 70 and 73–74.

The leuco-indophenols prepared according to the invention are preferably sulphurized by the boiling melt process.

EXAMPLE 1

210 g (1 mol) of 3-amino-9-ethyl-carbazole, 220 g (2 mols) of p-hydroquinone and 2 g of iodine are stirred at 180° to 200° C. under nitrogen for about 16 hours and the water of reaction is distilled off (about ~8 ml). The excess p-hydroquinone (boiling point$_{0.55\ mbar}$:140° C.) is then distilled off at a bath temperature of 200° to 220° C. and under a pressure of 0.55 mbar.

Yield: 330 g of crude product consisting of 3-(4-hydroxy-anilino)-9-ethyl-carbazole=110% yield, relative to 3-amino-9-ethyl-carbazole employed, that is to say the product also contains about 10% of p-hydroquinone.

If further purification is desired, the product can be distilled in vacuo. Boiling point$_{0.25\ to\ 0.55\ mbar}$:280° C. (bath temperature of 320° to 340° C.)

If the batch is reacted without iodine, a product is obtained which, according to the thin layer chromatogram (running agent: toluene/ethyl acetate 1:1), is less pure; elementary analysis shows no differences.

If 3-amino-9-octyl-carbazole is employed instead of 3-amino-9-ethyl-carbazole, 3-(4-hydroxy-anilino)-9-octyl-carbazole is obtained in a comparable manner.

EXAMPLE 2

450 g (2.47 mols) of 3-aminocarbazole, 500 g (4.55 mols) of p-hydroquinone and 5 g of iodine are stirred at 210° to 230° C. under nitrogen for about 16 hours and the water of reaction is distilled off. The reaction is continued until no further 3-aminocarbazole can be detected in the thin layer chromatogram (running agent: toluene/ethyl acetate 1:1). The excess p-hydroquinone is then distilled off in vacuo (0.55 mbar). Yield: 540 g of crude 3-(4-hydroxy-anilino)-carbazole; the product is sufficiently pure for the preparation of the desired sulphur dyestuff. If further purification is desired, the product can be distilled in vacuo: boiling point $_{0.13\ mbar}$:~310° C.

If less p-hydroquinone is employed, a less pure product which gives duller dyestuffs is obtained.

If the reaction is carried out in the presence of decalin, this solvent can simultaneously serve as an entraining agent for the water of reaction.

EXAMPLE 3

200 g (1.83 mols) of p-aminophenol, 2 g of iodine and 200 g (1.1 mols) of 3-aminocarbazole are stirred at 240° C. under nitrogen for 18 hours. Ammonia is split off and the excess p-aminophenol is then distilled off. 260 g of 3-(4-hydroxy-anilino)-carbazole which, according to the thin layer chromatogram, is contaminated with a little 4,4'-dihydroxy-diphenylamine are obtained. However, this impurity does not interfere with the preparation of the known sulphur dyestuff.

If 3-amino-9-ethyl-carbazole is employed instead of 3-amino-carbazole, 3-(4-hydroxy-anilino)-9-ethyl-carbazole is obtained in a similarly good way.

EXAMPLE 4

115 g (1.05 mols) of p-hydroquinone, 180 g (0.99 mol) of 3-aminocarbazole, 30 ml of dimethyldiglycol (diglycol dimethyl ether) and 1 g of iodine are heated to 220° C. under nitrogen for 7 hours and a total of 50 ml (water of reaction+dimethyldiglycol) is distilled off over a small column. The yield of 3-(4-hydroxy-anilino)-carbazole is virtually quantitative.

EXAMPLE 5

210 g (1 mol) of 3-aminoethyl-carbazole, 155 g (1.4 mols) of p-hydroquinone, 2 g of iodine and 60 ml of decalin are heated to 210° C. (bath temperature) under nitrogen, and whilst stirring, for 9 hours, the water of reaction and the decalin being distilled off over a short column in the course of the reaction. The excess of p-hydroquinone is then distilled off under reduced pressure. The yield of 3-(4-hydroxy-anilino)-carbazole of 303.5 g is virtually quantitative.

EXAMPLE 6

210 g (1 mol) of 3-amino-9-ethyl-carbazole, 176 g (1.6 mols) of p-hydroquinone, 44 g (0.4 mol) of p-aminophenol and 2 g of iodine are stirred at 170° to 180° C. under nitrogen for 14 hours, the water of reaction and ammonia being distilled off. The excess of p-hydroquinone and p-aminophenol is then distilled off under 0.4 mbar. Yield: 325 g of crude 3-(4-hydroxy-anilino)-9-ethyl-carbazole which, if desired, can be further purified by distillation under reduced pressure.

We claim:

1. The process for the preparation of a 3-(4-hydroxyanilino)-carbazole of the formula

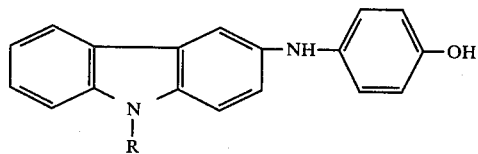

wherein R is hydrogen, alkyl having 1 to 8 carbon atoms or halogenalkyl having 1 to 8 carbon atoms, comprising reacting a 3-aminocarbazole of the formula.

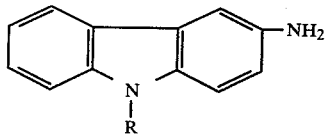

with p-hydroquinone or p-aminophenol or a mixture of p-hydroquinone and p-aminophenol in at least stoichiometric amounts by heating to a temperature of 150° to 300° C. with exclusion of oxygen.

2. The process according to claim 1 wherein the reactants are heated to a temperature of 170° to 230° C.

3. The process according to claim 1 wherein the reaction is carried out in the presence of catalytic amounts of iodine.

4. The process according to claim 3 wherein the reaction is carried out in the presence of 0.1 to 4% by weight of iodine, relative to the 3-aminocarbazole reactant.

5. The process according to claim 1 wherein the p-aminophenol or p-hydroquinone amounts to at least 1.3 times the stoichiometric reaction amount.

6. The process according to claim 1 wherein the p-aminophenol or p-hydroquinone amounts to at least 1.6 times the stoichiometric reaction amount.

7. The process according to claim 1 wherein the reaction is carried out in the presence of an inert solvent.

8. The process according to claim 7 wherein the reaction is carried out in the presence of up to 15% by weight solvent.

* * * * *